(12) United States Patent
Cain et al.

(10) Patent No.: US 8,863,333 B2
(45) Date of Patent: Oct. 21, 2014

(54) PORTABLE IV POLE AND LITTER

(71) Applicant: North American Rescue, LLC, Greer, SC (US)

(72) Inventors: Christopher Cain, Raeford, NC (US); Joanne S. Walter, Blue Ridge, GA (US)

(73) Assignee: North American Rescue, LLC, Greer, SC (US)

(*) Notice: Subject to any disclaimer, the term of this patent is extended or adjusted under 35 U.S.C. 154(b) by 218 days.

(21) Appl. No.: 13/707,205

(22) Filed: Dec. 6, 2012

(65) Prior Publication Data

US 2013/0145554 A1 Jun. 13, 2013

Related U.S. Application Data

(60) Provisional application No. 61/568,555, filed on Dec. 8, 2011.

(51) Int. Cl.
| | |
|---|---|
| *A47B 1/00* | (2006.01) |
| *A47C 31/00* | (2006.01) |
| *A61G 1/013* | (2006.01) |
| *A61M 5/14* | (2006.01) |
| *A61G 1/04* | (2006.01) |

(52) U.S. Cl.
CPC ............ *A61G 1/013* (2013.01); *A61M 5/1415* (2013.01); *A61M 5/1417* (2013.01); *A61G 1/04* (2013.01); *A61M 2209/082* (2013.01); *A61M 2209/084* (2013.01)
USPC .................................................. 5/626; 5/658

(58) Field of Classification Search
USPC ............ 5/110, 11, 503.1, 625–629, 658, 662; 248/125.8, 161, 159
See application file for complete search history.

(56) References Cited

U.S. PATENT DOCUMENTS

| | | | | |
|---|---|---|---|---|
| 273,287 | A | * | 3/1883 | Johnstone .......................... 5/627 |
| 709,332 | A | * | 9/1902 | Koons ................................ 5/116 |
| 1,205,186 | A | * | 11/1916 | Fuchs ................................ 5/627 |
| 1,865,757 | A | * | 7/1932 | Honsowetz .................... 211/172 |
| 2,276,256 | A | * | 3/1942 | Visness et al. ................... 403/97 |
| 2,511,061 | A | * | 6/1950 | Hughes ............................. 5/627 |
| 2,593,567 | A | * | 4/1952 | Keck ....................... 211/119.006 |
| 2,841,634 | A | * | 7/1958 | Kimball .......................... 52/632 |
| 2,982,572 | A | * | 5/1961 | Farber ........................... 403/219 |
| 3,007,180 | A | * | 11/1961 | Zaugg .............................. 5/625 |
| 3,426,367 | A | * | 2/1969 | Bradford ........................... 5/626 |
| 3,698,564 | A | * | 10/1972 | Muller ..................... 211/119.003 |
| 3,709,556 | A | * | 1/1973 | Allard et al. ................ 297/188.2 |
| 3,835,486 | A | * | 9/1974 | Benoit et al. .................... 5/503.1 |

(Continued)

*Primary Examiner* — William Kelleher
*Assistant Examiner* — Eric Kurilla
(74) *Attorney, Agent, or Firm* — McNair Law Firm, P.A.; Douglas W. Kim

(57) ABSTRACT

A portable litter with an integrated IV pole comprising: a frame having a handle section; a storage cavity defined in the handle section; a handle grip extendably attached to the handle section that can be retracted into the storage cavity or extended out of the storage cavity; an end cap removably secured to the handle grip having an IV pole retaining assembly; an IV pole having a standard that can be secured to the end cap by the retaining assembly, received in an opening defined in the handle grip and received in the storage cavity when the IV pole is in a collapsed configuration; and, a support arm rotatably attached to the standard that is parallel to the standard when the IV pole is in a collapsed configuration and rotated generally perpendicular to the standard when the IV pole is in an operational position.

17 Claims, 11 Drawing Sheets

(56) References Cited

U.S. PATENT DOCUMENTS

| | | | | |
|---|---|---|---|---|
| 3,935,603 A | * | 2/1976 | Bryant | 5/11 |
| 4,225,104 A | * | 9/1980 | Larson | 248/125.8 |
| 4,262,872 A | * | 4/1981 | Kodet | 248/311.3 |
| 4,541,596 A | | 9/1985 | Price | |
| 4,584,989 A | * | 4/1986 | Stith | 600/18 |
| 4,807,837 A | * | 2/1989 | Gawlik et al. | 248/125.8 |
| 5,179,746 A | | 1/1993 | Rogers | |
| 5,217,315 A | * | 6/1993 | Rosane | 403/102 |
| 5,332,184 A | | 7/1994 | Davis | |
| 5,497,966 A | * | 3/1996 | Fuhrmann | 248/161 |
| 5,598,592 A | * | 2/1997 | Castellani | 5/627 |
| 5,876,016 A | * | 3/1999 | Urban et al. | 248/159 |
| 5,924,658 A | * | 7/1999 | Shiery et al. | 248/125.8 |
| 5,987,673 A | * | 11/1999 | Smith | 5/627 |
| 6,109,572 A | * | 8/2000 | Urban et al. | 248/159 |
| 6,361,002 B1 | * | 3/2002 | Cheng | 248/161 |
| 6,431,505 B2 | * | 8/2002 | Chinn et al. | 248/121 |
| 6,443,157 B1 | * | 9/2002 | Sargent | 128/870 |
| 6,907,632 B2 | * | 6/2005 | Bourgraf, Jr. | 5/627 |
| 7,412,735 B2 | | 8/2008 | McDaniel et al. | |
| 7,506,775 B2 | * | 3/2009 | Hartzell et al. | 220/1.5 |
| 8,038,330 B2 | * | 10/2011 | Liu | 362/413 |
| 8,087,112 B2 | * | 1/2012 | Cahaan | 5/625 |
| 8,327,482 B2 | * | 12/2012 | Awerbuch et al. | 5/627 |
| 8,443,472 B2 | * | 5/2013 | Sherman et al. | 5/503.1 |
| 8,567,730 B1 | * | 10/2013 | Stevenson | 248/125.8 |
| 8,739,335 B1 | * | 6/2014 | Hoggatt | 5/626 |
| 2002/0011543 A1 | | 1/2002 | Chinn et al. | |
| 2002/0104934 A1 | * | 8/2002 | Elliott et al. | 248/126 |
| 2005/0028283 A1 | * | 2/2005 | Castellani et al. | 5/627 |
| 2005/0210589 A1 | * | 9/2005 | Dimentmen | 5/627 |
| 2006/0059625 A1 | * | 3/2006 | Kotitschke | 5/625 |
| 2006/0230540 A1 | * | 10/2006 | Whelan | 5/662 |
| 2010/0138999 A1 | * | 6/2010 | Westmoreland, II et al. | 5/627 |
| 2010/0146702 A1 | | 6/2010 | Sherman et al. | |
| 2010/0230558 A1 | | 9/2010 | Knubley | |
| 2012/0066836 A1 | * | 3/2012 | Kaarstein et al. | 5/627 |
| 2013/0086748 A1 | * | 4/2013 | Walter et al. | 5/627 |

* cited by examiner

PORTABLE IV POLE AND LITTER

CLAIM OF PRIORITY

This application claims priority on U.S. Provisional Patent Application Ser. No. 61/568,555 filed on Dec. 8, 2011.

FIELD OF THE INVENTION

This invention is directed to a portable intravenous (IV) treatment support apparatus and more specifically, to a litter IV pole combination for storage of the IV pole within the litter allowing the IV pole to be removed from storage and deployed for use supported by said litter.

BACKGROUND OF THE INVENTION

Historically, IV poles and stands are independent apparatus and are positioned beside a bed or litter. Improvements then were made so that the IV pole could be mounted to the bed or litter. To improve storage and transportation, the poles were made to telescope thereby allowing a shorter apparatus for storage and transportation that can be extended to its full length when used to hold an IV bag.

The hooks at the top of the pole generally radiate away from the pole and when stored or transported, can snag clothing or otherwise interfere with the treatment of the injured patient. For example, U.S. Pat. No. 5,179,746 describes an IV pole pivotally connected to a stretcher having an extendable pole and an IV hook. The hook, however, can be exposed and interfere with the treatment of the patient when the IV pole is in a stored position. United States Patent Application Publication 2002/0011543 also shows a pole pivotally connected to a side rail of an emergency stretcher, but includes an extended portion that can, again, snag clothing, IV lines, tubes and other items, and interfere with treating the patient as shown in FIG. 8.

Other attempts to provide an IV pole with a stretcher include United States Patent Application Publication 2010/0146702 which describes a clamp apparatus for securing the pole to the stretcher. This design is overly complex and includes multiple points that could snag clothing and the like. Further, the clamp apparatus itself is prone to being misplaced and therefore preventing the IV pole from being attached to the stretcher. U.S. Pat. No. 5,332,184 further illustrates the disadvantages of using an independent clamp to secure an IV pole to a stretcher as this apparatus is also easily prone to being misplaced. U.S. Pat. No. 7,412,735 illustrates a complex patient support apparatus having openings in end portions for receiving an IV pole. However, the positioning of the IV pole requires that the bag hang at the head or foot of the patient resulting in IV lines longer than necessary, lines that can be snagged, and a greater distance between the IV bag (and needed fluid) and the patient.

There have also been attempts to make an IV pole that is designed for battlefield use. United States Patent Application Publication 2010/0230558 is directed to a pole for supporting an intravenous bag for use in the field on uneven or soft terrain. The pole has a pointed tip which may be pressed into soft ground, mud, tundra or ice. This application discloses an IV pole having a bag support member, a pole and a pole support member with a pointed tip. In use, the bag support member is attached to the upper end of the pole, the pole support member is attached to the lower end of the pole and the pole is held erect by pushing the pointed tip into the terrain. This design, results in the IV pole being stored separately from the litter. It would be advantageous for the IV pole to be stored with the litter rather than as a separate item so that the IV pole is less apt to be misplaced thereby depriving the treating individual of medical equipment needed for the patient.

Accordingly, an object of the present invention is to provide an IV pole that can be stored integrally with a litter while being easy to deploy.

It is another object of the present invention to provide an IV pole that can be easily attached to a litter in a position in near proximity to the IV insertion point which can be the hand, arm or even for central IV lines.

It is another object of the present invention to provide an IV pole that reduces or eliminates the risk of snagging when stored or deployed.

SUMMARY OF THE INVENTION

The above objectives are accomplished according to the present invention by providing a portable litter with an integrated IV pole comprising: a frame having a handle section; a storage cavity defined in said handle section; a handle grip extendably attached to said handle section that can be retracted into said storage cavity or extended out of said storage cavity; an end cap removably secured to said handle grip having an IV pole retaining assembly; an IV pole having a standard that can be secured to said end cap by said retaining assembly, received in an opening defined in said handle grip and received in said storage cavity when said IV pole is in a collapsed configuration; and, a support arm rotatably attached to said standard that is parallel to said standard when said IV pole is in a collapsed configuration and rotated generally perpendicular to said standard when said IV pole is in an operational position.

The invention can also include a hinge attached to said handle section; and, a standard receiving opening defined in said hinge for receiving said IV pole when said IV pole is in said operational position. An end stop can be included in said standard preventing said standard from being received in said retaining assembly past a predetermined distance. A notch can be defined in said support arm at an end distal to said standard for supporting an IV bag. The support arm can rotate into a position about 90° to said standard when said IV pole is in said operational position.

The standard can include a slot for receiving said support arm so that said support arm is flush in said upper section in said collapsed configuration and extended to about 90° in relation to said standard in said operational position for supporting an IV bag. A stop pin can be carried by said support arm preventing said support arm from rotating more than about 270° from said collapsed configuration to said operational position. The standard can include an upper section and a lower section telescopically attached providing for a standard that can vary in length. A friction locking system can be included to secure the upper and lower section at a fixed height.

DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
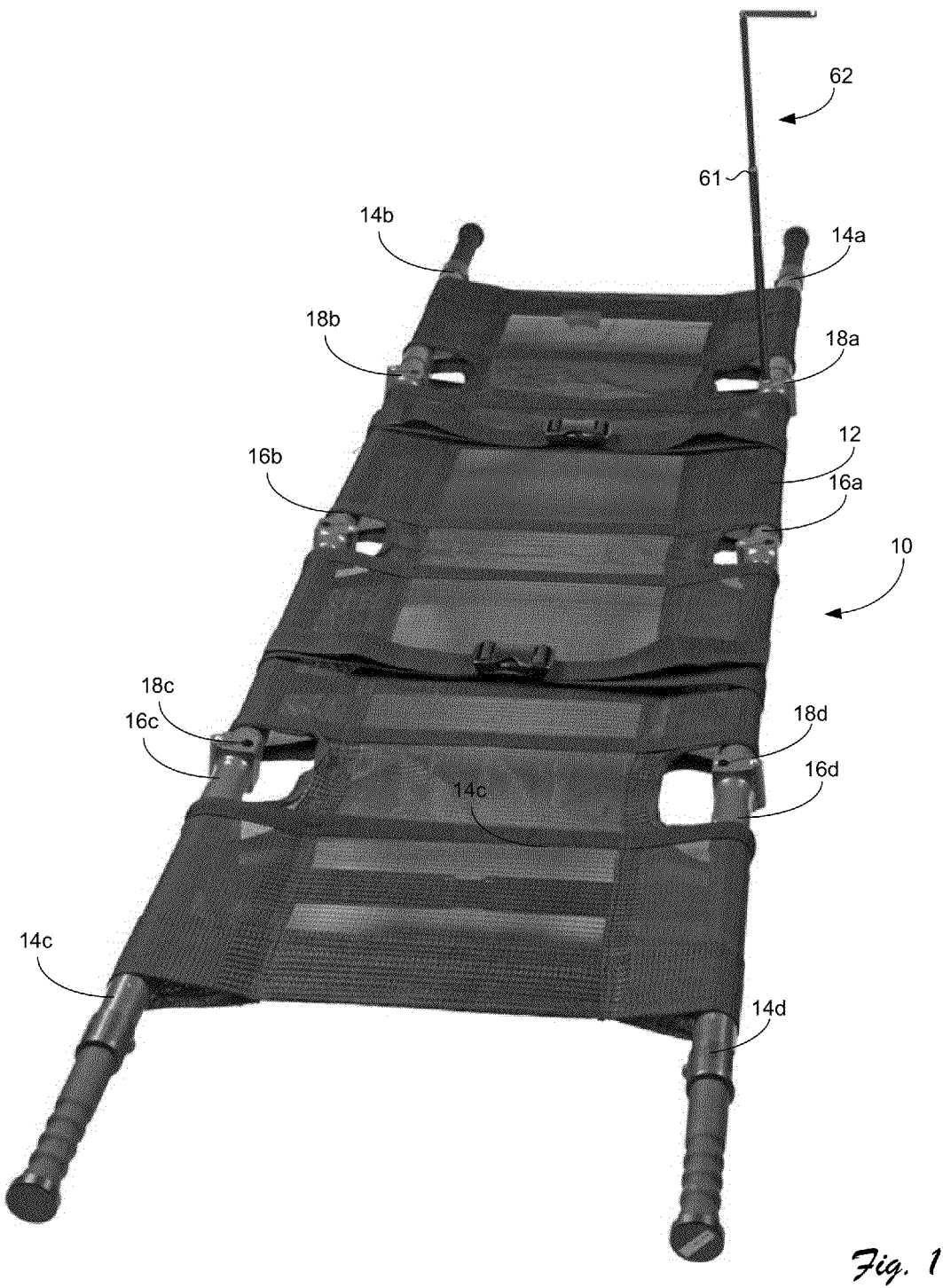
FIG. 1 is a drawing of the invention.
Figure 2:
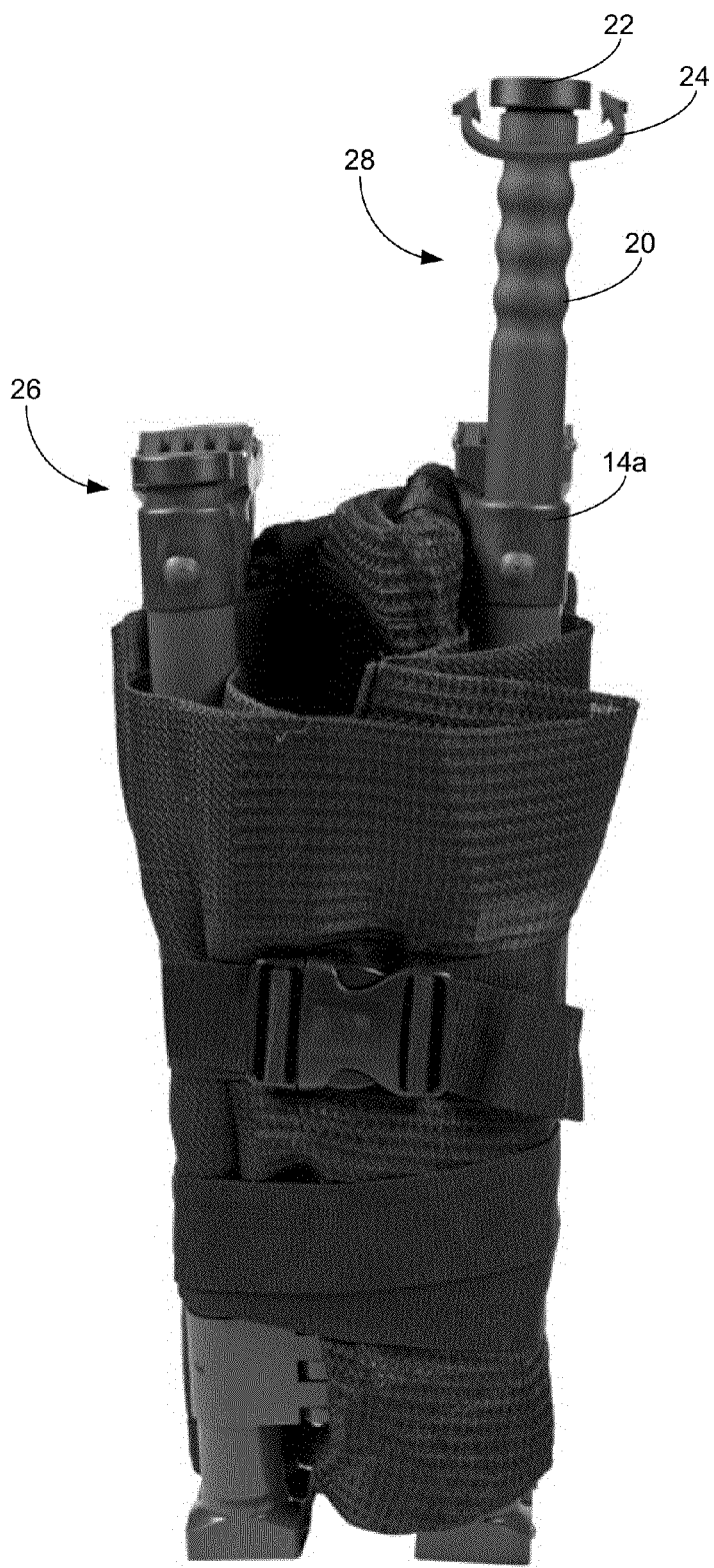
FIG. 2 is a drawing of the invention.

Referring to FIG. 1, a litter 10 having a tent 12 and a frame. The frame can include handle sections 14a through 14d and mid sections 16a through 16d. There are hinges 18a through 18d between the various handle sections and mid sections allowing the frame to be collapsed or extended. The litter, in its extended position as shown in FIG. 1, allows a patient to lie on the tent and be transported by other individuals using the handles or when the litter is placed on a rack such as in a vehicle or aircraft. In one embodiment, the litter is part of a portable kit or vehicle kit that includes the litter and other first responder medical supplies. One such kit is the Warrior Aid and Litter Kit (WALK) provided by North American Rescue, LLC, which includes medical supplies as the Talon II 90C, Black Talon® Nitrile Trauma Gloves, Nasopharyngeal Airway 28F with Lubricant, HyFin Chest Seal, ARS® Needle Decompression Kit, Combat Application Tourniquet, Trauma Dressing, S-Rolled Gauze, ETD Abdominal Emergency Trauma Dressing, SAM Splint II, Trauma Shears and Surgical Tape. These items are contained in a bag with various compartments and to allow the litter to be included, the litter can be arranged in a folded storage configuration (as shown in FIG. 2) for storage and transportation and expanded to an operation configuration when in use (as shown in FIG. 1). The hinges 18a through 18d allow for the litter to be transitioned between the storage and transportation configuration to the operational configuration.

Referring to FIG. 2, in one embodiment, at least one handle section includes a storage cavity internal to the handle section. The internal cavity can extend along the handle grip and into the handle section. An end cap 22 can be removably attached to handle grip 20 so that when moved in direction 24, the end cap can be secured to or removed from the handle grip. In one embodiment, the handle grip can be received by the handle section so that the handle grip is enclosed by the handle section in a closed position as shown by 26. When the handle grip is extended, as shown by position 28, the handle grip can be used to hold the litter or place the litter on a rack.

Figure 3A:
FIGS. 3A and 3B are a drawing of the invention.
Figure 3B:
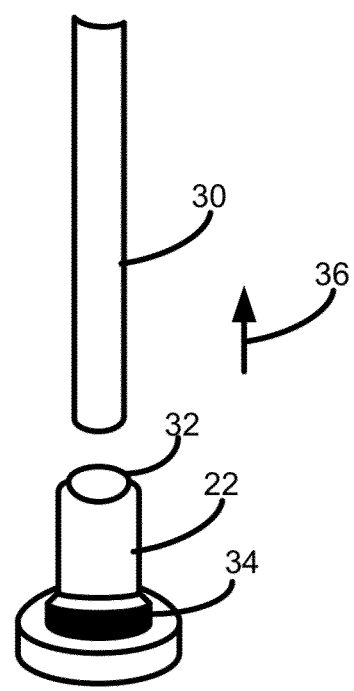

Referring to FIGS. 3A and 3B, the end cap has been removed from handle section 14a and handle grip 20. The end cap carries IV pole 30 which is received in an IV pole retaining assembly 32.

The end cap can be secured to the handle grip through threads 34. The IV pole can be removed from the end cap simply by lifting the IV pole from the end cap in a direction shown as 36. In one embodiment, the IV pole is secured to the end cap through a retaining assembly that includes a detent system allowing the IV standard to be pulled from the end cap, but held in the end cap until sufficient force is used to pull the IV standard from the end cap. In one embodiment, the IV standard is held in the end cap through a friction fitting. In one embodiment, the IV standard is secured to the retaining assemble of the end cap through threads, detent, bayonet connection, BNC connection, pin-slot connection and the like.

Figure 4:
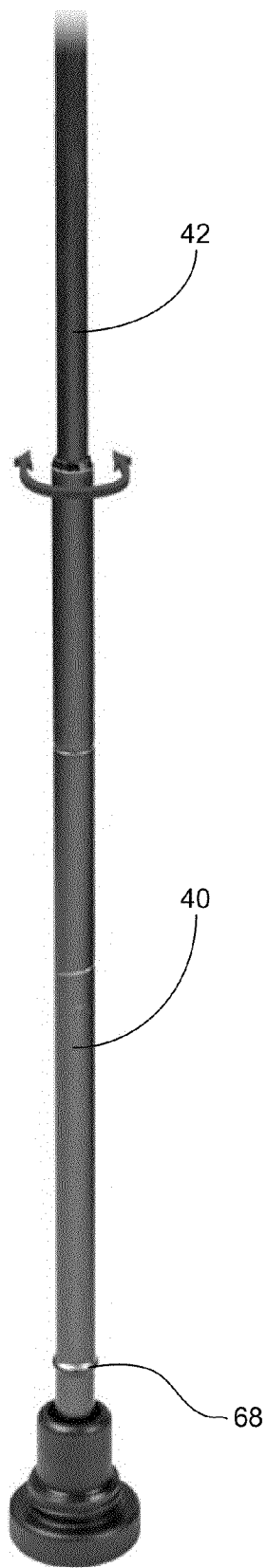
FIG. 4 is a drawing of the invention.

Referring to FIG. 4, the IV pole is shown in more detail. Since the IV pole length is limited generally by the inner cavity of the handle section and the handle section length is limited due to the need to fold the litter into a storage or transportation configuration, the IV pole can collapse into a length that fits in the handle section. The IV pole can include multiple sections such as lower section 40 and upper section 42 constructed in a telescopic arrangement. The two IV pole sections can be friction fit so that when extended, upper and lower sections remain extended to provide a length greater than any one section alone. In one embodiment, the IV pole includes a telescoping friction locking system having the upper section twisted to form a friction fit with the lower section due to an extending projection carried by the upper or lower section creating friction when twisted locking the two sections in a fixed position. The friction between the upper and lower sections can be in interference fitting arrangement so that when twisted in the unlocking direction, the upper and lower sections can be collapsed together for storage and transportation.

In one embodiment, several IV pole sections can be contained in one or more handle sections so that once removed from the litter, the IV pole section can be assembled to provide an IV pole with a length greater than one IV pole section and greater than the length of the handle section.

Figure 5A:
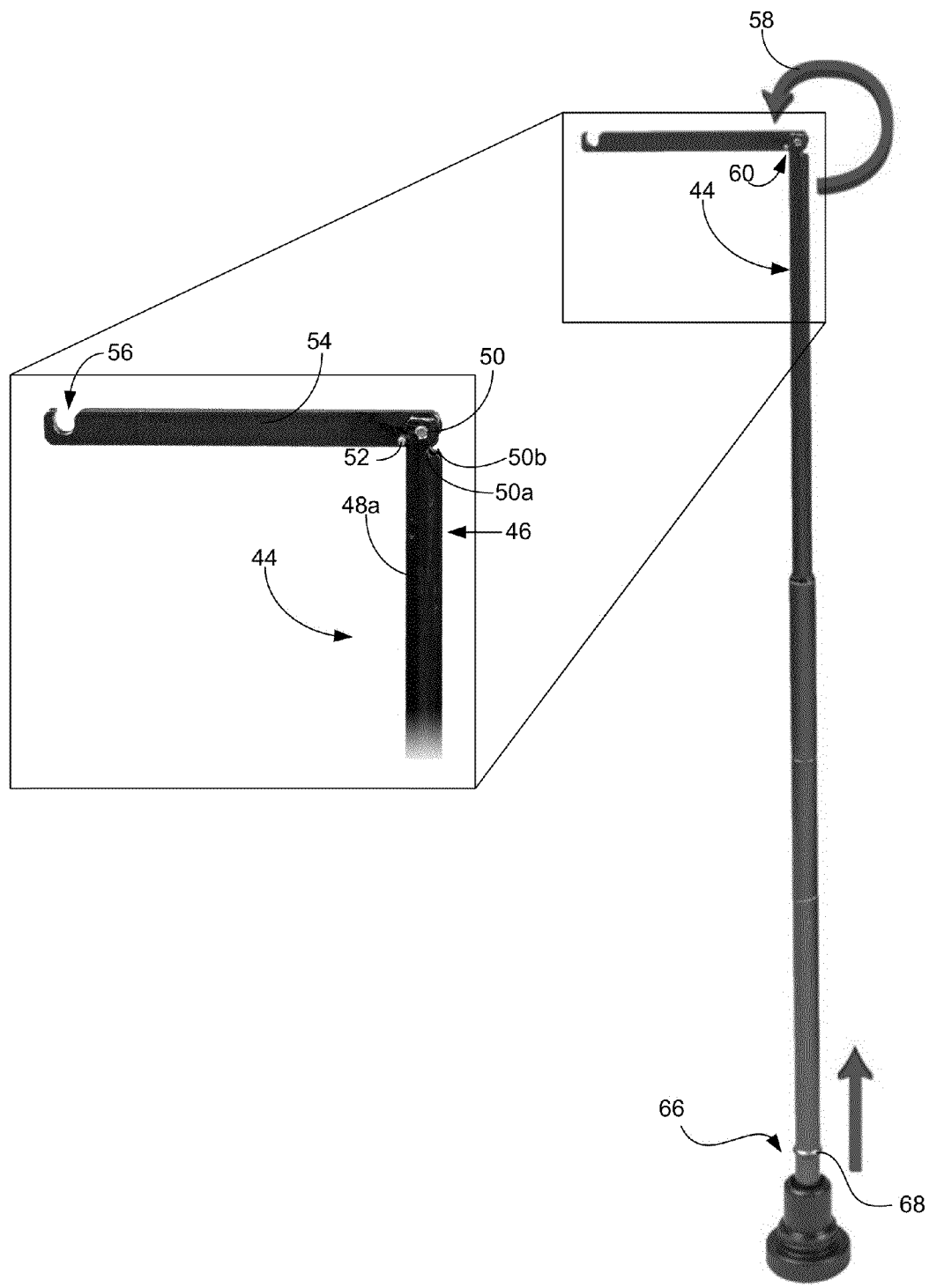
FIGS. 5A through 5C are drawings of a portion of the invention.
Figure 5B:
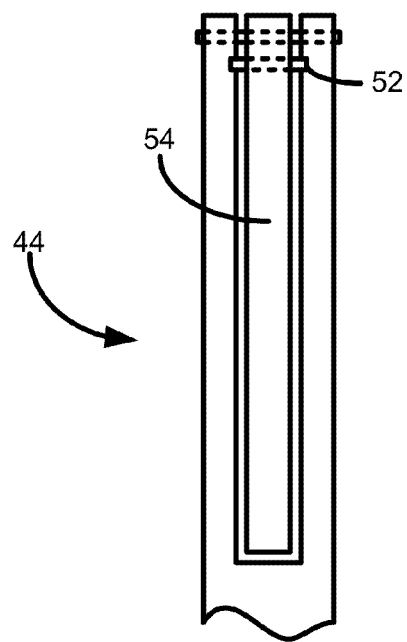
Figure 5C:
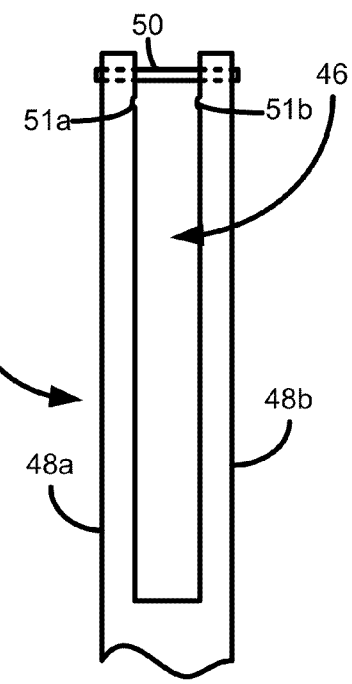
Figure 6:
FIG. 6 is a drawing of the invention.

The distal end of the IV pole is shown in more detail in FIGS. 5B and 5C. The distal end 44 includes a slot 46 defined between standards 48a and 48b. Pin 50 can be placed between the standards and received in openings defined in the standards. Notches 51a and 51b are defined in the standard and can receive a stop pin. The stop pin 52 is included in support arm 54 rotatably attached to the standards through pin 50. Notch 56 can be included in the support arm for hanging items such as an IV bag from the arm.

Figure 7:
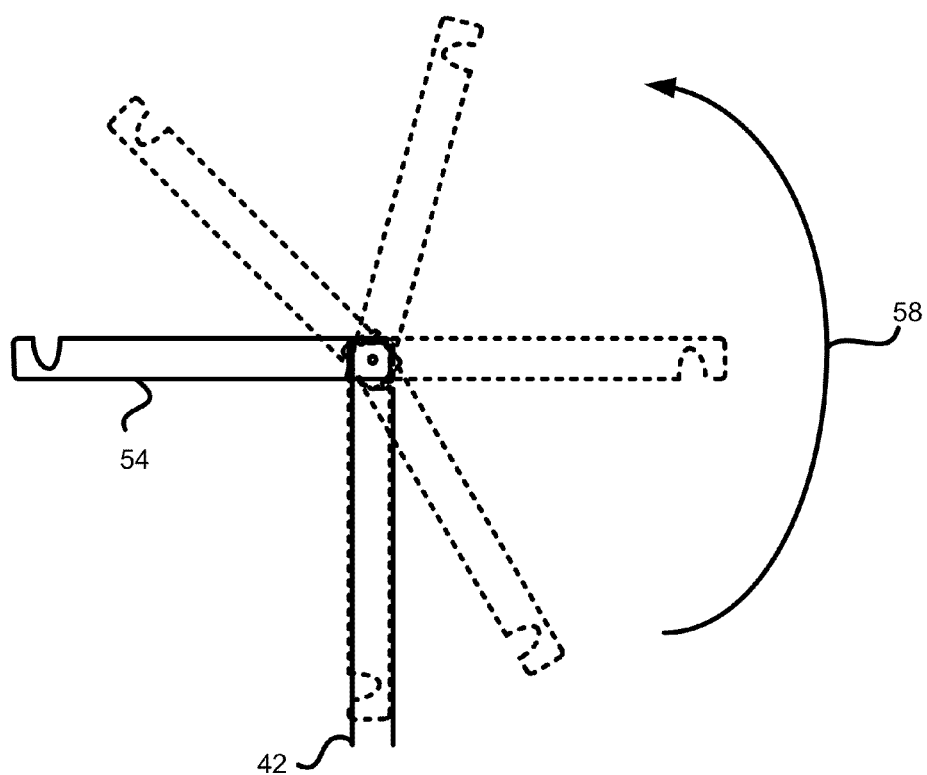
FIG. 7 is a drawing of the invention.

The support arm can rotate to be received flush with the standards as shown in FIG. 3A. Further, the support arm, along with the upper section 42, are received within the lower section when in the collapsed position. The stop pins are received in notches allowing the support arm and standard to be flush so that they can be received in the lower section. Various stages of extension of the support arm are shown in FIG. 7.

Once extended, the entire support arm is extended past the lower section and can be rotated in a direction shown as 58 (FIG. 5A) so that the stop pins contact the side of the standards generally shown at 60 and opposite the notches side of the standards to secure the support arm in generally a 90° angle to the upper section. This configuration allows an IV bag to be supported above the patient as variable heights while allowing it be to collapsed and inserted into the handle section for storage and transportation.

In one embodiment, the IV pole can be attached to the litter as shown in FIG. 1. IV pole 62 is carried by hinge 18a as shown. The hinge includes a standard receiving opening 64 that can receive a proximal end 66 (FIG. 5A) of the IV pole so that the IV pole is held generally perpendicular to the handle section of the litter. Multiple standard receiving openings can be located throughout the litter in the operational arrangement as each hinge can include a standard receiving opening. This feature allows the IV pole to be placed closest to the IV entry location on the patient. Further, multiple IV poles can be used as a litter with three hinges per side and would include six IV pole standard receiving openings for holding six IV poles. The IV pole can include a proximal end stop 68 to prevent the IV pole from dropping too far into the standard receiving opening thereby maintaining a predetermined height of the lower section of the IV pole. The IV pole can include a standard 61 and a support arm 54.

Figure 8A:
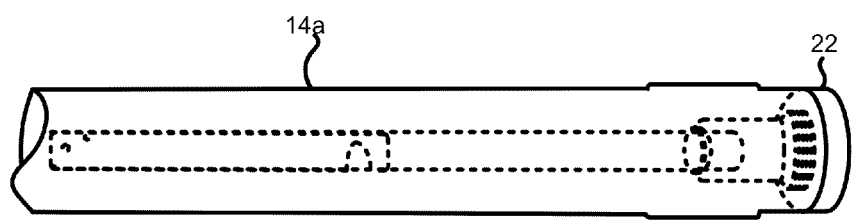
FIGS. 8A and 8B are side views of aspects of the invention.
Figure 8B:
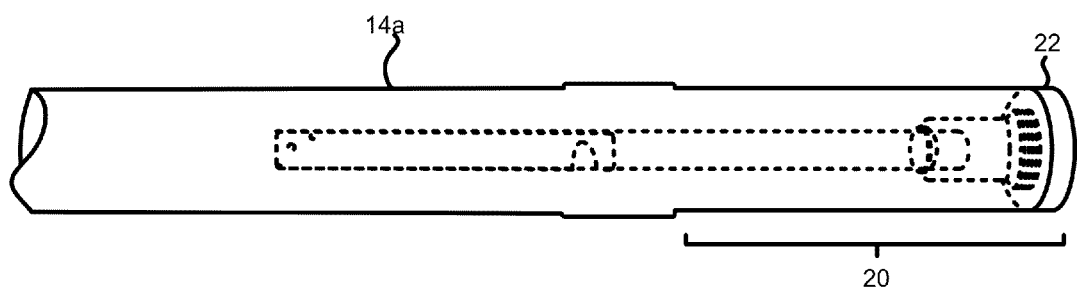
Figure 9A:
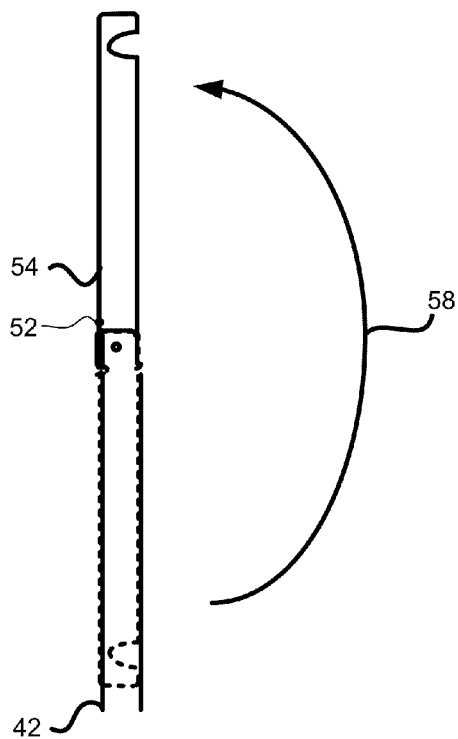
FIGS. 9A and 9B are side views of aspects of the invention.
Figure 9B:
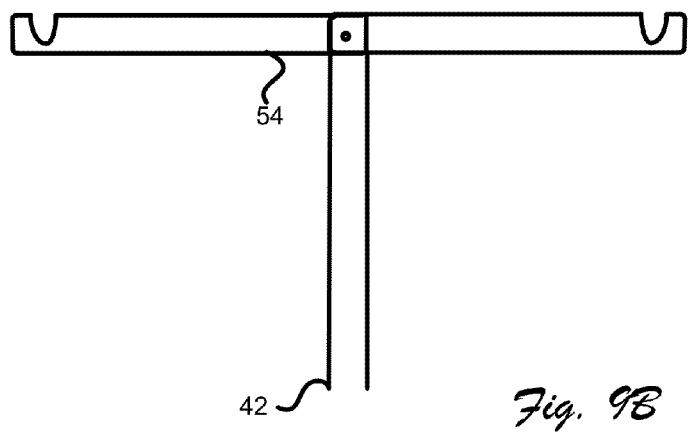

Referring to FIG. 8A, the IV pole is shown in the stored configuration with the proximal end of the IV pole secured to the end cap and the end cap secured to the handle grip 70 which is attached to the handle section of the litter. The handle grip is retracted within the handle section. The IV pole is received in the handle section. When the handle is extended from the handle section, the IV pole remains secured to the end cap allowing the IV pole to be removed from the handle section when the end cap is removed as the IV pole, secured to the end cap, will be retrieved form the handle section by removing the end cap. The IV pole in FIGS. 8A and 8B are shown in a collapsed configuration for storage while FIG. 1 shown the IV pole in an operational configuration In one embodiment, the invention can support multiple IV bags. Referring to FIGS. 9A and 9B, the support arm is rotatably connected to the standard at generally at a mid-point of the support arm. In the collapsed configuration, the support arm is parallel to the standard with a portion of the support arm received in the slot of the standard as shown in FIG. 9A. It should be noted that the support arm can be rotatably attached to the standard on one side of the standard and not necessarily received in a slot defined in the support arm. In operation, the support arm can be rotated in a direction shown at 58 about 90° and stopped with stop pin 52 so that the support arm is perpendicular to the standard.

While a preferred embodiment of the invention has been described using specific terms, such description is for illustrative purposes only, and it is to be understood that changes and variations may be made without departing from the spirit or scope of the following claims.

What is claimed is:

1. A portable litter with an integrated IV pole comprising:
a frame having a handle section;
a storage cavity defined in said handle section;
a handle grip extendably attached to said handle section that can be retracted into said storage cavity or extended out of said storage cavity;
an end cap removably secured to said handle grip having an IV pole retaining assembly;
an IV pole having a standard that can be secured to said end cap by said retaining assembly, received in an opening defined in said handle grip and received in said storage cavity when said IV pole is in a collapsed configuration; and,
a support arm rotatably attached to said standard that is parallel to said standard when said IV pole is in a collapsed configuration and rotated generally perpendicular to said standard when said IV pole is in an operational position.

2. The apparatus of claim 1 including:
a hinge attached to said handle section; and,
a standard receiving opening defined in said hinge for receiving said IV pole when said IV pole is in said operational position.

3. The apparatus of claim 1 including an end stop included in said standard preventing said standard from being received in said retaining assembly past a predetermined distance.

4. The apparatus of claim 1 including a notch defined in said support arm at an end distal to said standard for supporting an IV bag.

5. The apparatus of claim 1 wherein said support arm rotates into a position about 90° to said standard when said IV pole is in said operational position.

6. The apparatus of claim 5 including a slot defined in said standard for receiving said support arm so that said support arm is flush in said upper section in said collapsed configuration and extended to about 90° in relation to said standard in said operational position for supporting an IV bag.

7. The apparatus of claim 5 including a stop pin carried by said support arm preventing said support arm from rotating more than about 270° from said collapsed configuration to said operational position.

8. The apparatus of claim 1 wherein said standard includes an upper section and a lower section telescopically attached providing for a standard that can vary in length.

9. The apparatus of claim 8 including a friction locking system securing the upper and lower section at a fixed height.

10. A portable litter with an integrated IV pole comprising:
a frame for supporting a tent and having a handle section;
a storage cavity defined in said handle section;
an end cap removably secured to said handle section for closing said storage cavity when said end cap is secured to said handle section;
an IV pole having a standard and a support arm rotatably attached to said standard that can be received in said storage cavity and secured in said storage cavity with said end cap when said IV pole is in a collapsed configuration;
a standard receiving opening defined in said handle section for receiving said standard and supporting said standard generally perpendicular to said handle section; and,
whereas said support arm is generally parallel to said standard when said IV pole is in said collapsed configuration and generally perpendicular to said handle assembly when said IV pole is in said operational position.

11. The apparatus of claim 10 including a hinge attached to said handle section connecting said handle section to a mid section providing for a collapsible frame.

12. The apparatus of claim 10 including an end stop included in said standard preventing said standard from being received in said standard receiving opening past a predetermined distance.

13. The apparatus of claim 10 including a notch defined in said support arm at an end distal to said standard for supporting an IV bag.

14. The apparatus of claim 10 including a slot defined in said standard for receiving said support arm so that said support arm is generally parallel to said standard in said collapsed configuration and generally perpendicular to said standard in said operational position for supporting an IV bag.

15. The apparatus of claim 10 wherein said standard includes an upper section and a lower section telescopically attached providing for a standard that can vary in length.

16. The apparatus of claim 15 including a friction locking system securing the upper and lower section at a fixed height.

17. The apparatus of claim 10 including a handle grip extendably received in said storage cavity.

* * * * *